United States Patent [19]

Konno et al.

[11] Patent Number: 4,501,149

[45] Date of Patent: Feb. 26, 1985

[54] MICRO FRACTURE DETECTOR

[75] Inventors: Junichi Konno, Oi; Yukihiro Ueda, Fuji; Hiroaki Niitsuma; Noriyoshi Chubachi, both of Sendai, all of Japan

[73] Assignee: Asahi Kasei Kogyo Kabushiki Kaisha, Osaka, Japan

[21] Appl. No.: 543,707

[22] Filed: Oct. 20, 1983

[30] Foreign Application Priority Data

Oct. 29, 1982 [JP] Japan ................................. 57-191335

[51] Int. Cl.³ .................... G01N 29/04; G06F 15/332
[52] U.S. Cl. ........................................ 73/587; 73/602; 364/576; 364/726
[58] Field of Search ............... 364/485, 576, 726; 73/587, 801, 602

[56] References Cited

U.S. PATENT DOCUMENTS

| | | | |
|---|---|---|---|
| 3,871,577 | 3/1975 | Avellar et al. | 364/726 |
| 4,041,461 | 8/1977 | Kratz et al. | 364/736 |
| 4,216,475 | 8/1980 | Johnson | 364/725 |
| 4,293,921 | 10/1981 | Smith, Jr. | 364/726 |
| 4,403,311 | 9/1983 | Tournois | 367/11 |

Primary Examiner—Howard A. Birmiel
Attorney, Agent, or Firm—Sughrue, Mion, Zinn, Macpeak & Seas

[57] ABSTRACT

An acoustic emission is detected by a pickup, and its output is converted by a A/D converter into a digital signal, which is provided to a fast Fourier transform processor. The fast Fourier transform processor comprises a cascade connection of a plurality of operation stages, each composed of first and second input memories, a third memory having stored therein a rotation vector and an arithmetic unit for performing a Butterfly operation through using the pipelined architecture. In each stage one of the first and second input memories and the third memory are read out and the Butterfly operation is carried out on the pipelined basis. The operation result is written into that one of the first and second input memories of the next operation stage which has not been read out; thus all the operation stages perform a pipelined operation as a whole. The power of a spectrum obtained as the operation result of the last operation stage is calculated, obtaining a signal corresponding to the acoustic emission.

11 Claims, 23 Drawing Figures

|     | J K | L | AS 1 | AS 2 | AS 3 | AS 4 | AS 5 | ST 1 | ST 2 | MUL |
|-----|-----|---|------|------|------|------|------|------|------|-----|
| D 1 | 1   |   |      |      |      |      |      |      |      |     |
| D 3 |     |   |      |      |      |      |      |      |      | 1   |
| D 4 |     | 1 |      |      |      |      |      |      |      |     |
| S 1 |     |   |      |      |      | 1    |      |      |      |     |
| S 2 |     |   | 1    |      |      |      |      |      |      |     |
| SUB |     |   | 1    | 1    |      |      |      |      |      |     |
| D 5 |     |   | 0 1 1 | 1 0 1 | 0 0 0 |      |      |      |      |     |
| D 6 |     |   | 0 1 1 | 1 0 1 | 1 1 1 |      |      |      |      |     |
| S 3 |     |   |      |      |      |      |      | 1    |      |     |
| S 4 |     |   |      |      |      |      |      |      | 1    |     |

| AS1 | AS2 | AS3 | INSTRUCTION |
|---|---|---|---|
| 0 | 1 | 1 | MUL ⟶ ACCB |
| 0 | 1 | 0 | MUL ⟶ ACCA |
| 1 | 0 | 1 | LR + ACCA ⟶ ACCB |
| 1 | 0 | 0 | LR + ACCB ⟶ ACCA, MUL + ACCA ⟶ ACCA |
| 1 | 1 | 1 | MUL − ACCB ⟶ ACCB, LR − ACCB ⟶ ACCB |
| 1 | 1 | 0 | LR − ACCA ⟶ ACCA |

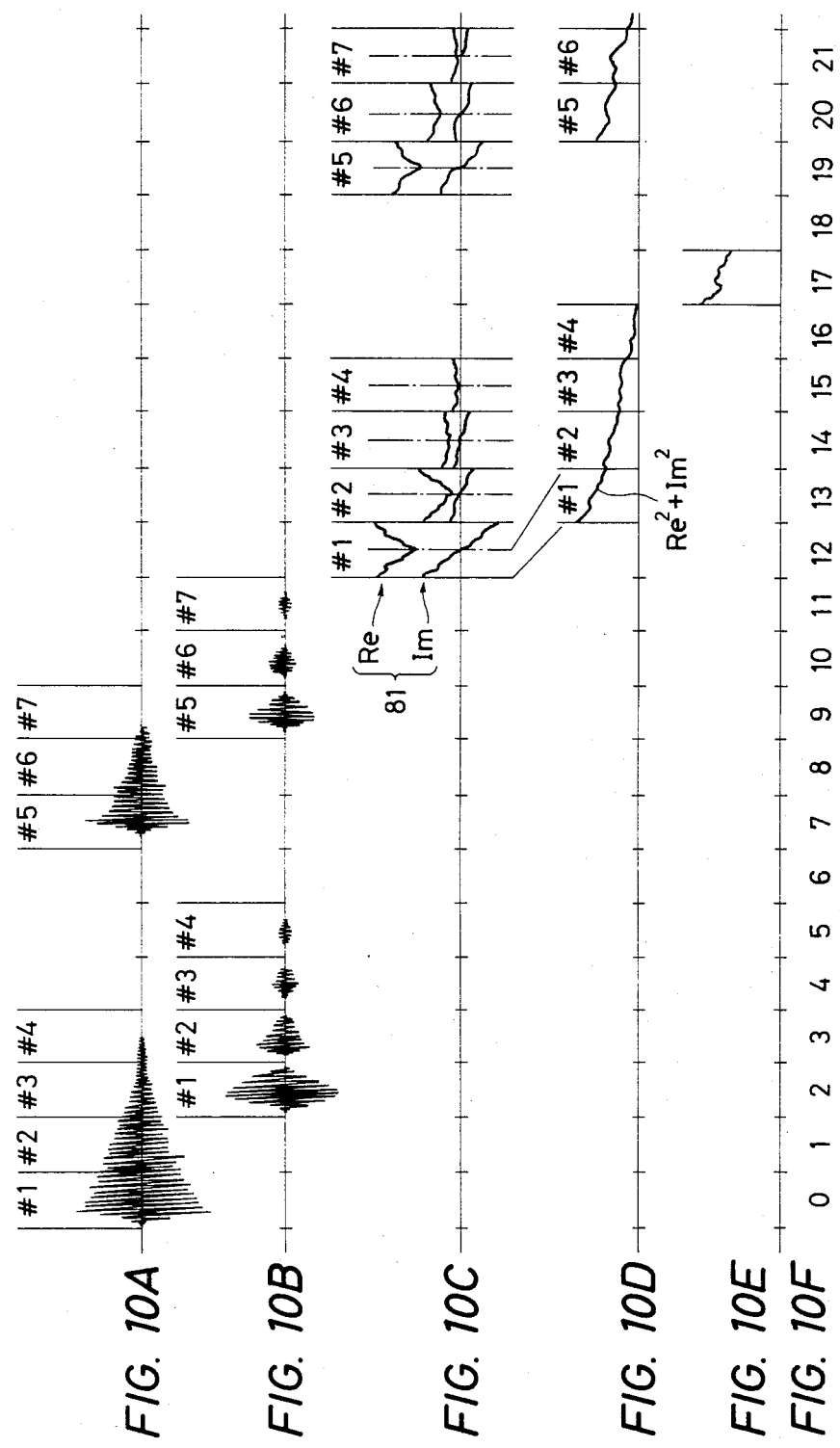

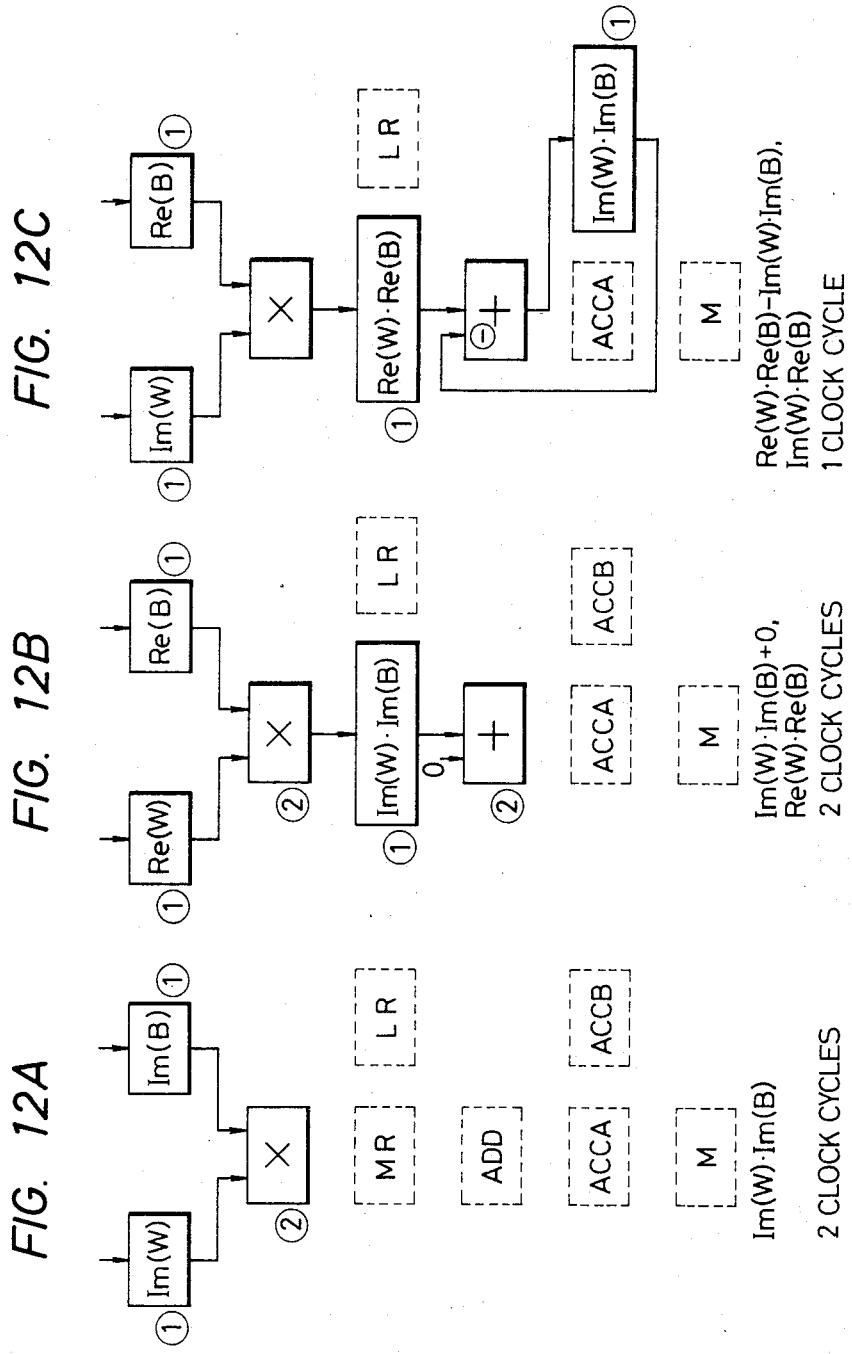

MICRO FRACTURE DETECTOR

BACKGROUND OF THE INVENTION

The present invention relates to an apparatus which senses an acoustic emission resulting from a micro fracture of an object, such as cracking, its growth, or fatigue, deterioration of the object, to detect its micro fracture.

The acoustic emission phenomenon is well-known in which when an object fractures microscopically, a part of its strain energy is emitted as ultrasonic waves, and this phenomenon has been utilized for detecting an abnormality of a material, equipment and the like by monitoring the acoustic emission (hereinafter referred to as AE) signal. But conventional detecting methods of this kind are intended primarily for measuring parameters in the time domain, that is, the intensity, the position of generation, the frequency of generation and the duration of the AE signal, and they encounter difficulty in removing external noises, such as a vibration sound and electrical noise, and call for a special circuit for discriminating between the noise and the AE signal.

There has also been proposed a method which, noting the difference in frequency spectrum between the AE signal and the external noise, discriminates between them on the basis of the difference between their attenuation factors by some filters of different frequency characteristics. This method does not aim at the frequency analysis and the discriminating filter cannot be designed unless the spectrum of the AE signal is preknown. Recently a method has been proposed which decides an abnormality by comparing the spectrum pattern of the AE signal and a reference spectrum pattern. Since the spectrum pattern of the AE signal undergoes substantial variations with the quality, the structure, the fracture process and so on of the object under inspection, it is very difficult to determine the reference spectrum pattern; therefore, there has been a strong demand for an apparatus which permits the real-time frequency analysis. In practice, however, there has not been proposed the processor that performs the real-time frequency analysis of the AE signal which has frequency components over as wide a frequency band as several ten KHz to 1 MHz.

SUMMARY OF THE INVENTION

It is therefore an object of the present invention to provide a micro fracture detector which permits a real-time frequency spectrum analysis of the AE signal to obtain a signal corresponding to a micro fracture of an object.

According to the present invention, the AE signal resulting from a micro fracture of an object under inspection is detected as an electric signal by means of a pickup, and the electric signal is amplified and sampled by an A/D converter, and each sampled value is converted into a digital signal. On the other hand, a plurality of stages are provided, each of which is comprised of first and second input memories, a third memory having stored therein a rotation vector and an arithmetic unit for performing a Butterfly operation on a pipelined basis. The digital signals from the A/D converter are written into the first and second input memories of the first stage alternately for each fixed number of samples and, in each stage, one of the first and second input memories and the third memory are read out, performing the Butterfly operation on the pipelined architecture. The operation result is written into that one of the first and second input memories of the next stage which has not been read out, thereby causing all the stages to perform the pipelined operation as a whole. The memories of each stage are accessed with a common address from address generating means. From each spectral component obtained as the operation result at the final stage is calculated its power component to obtain a signal corresponding to the micro fracture, which signal is used for detecting the micro fracture of the object under inspection.

With the above pipelined operation, it is possible to obtain the spectrum, with exponent and mantissa parts separate of each other, by fast Fourier transform means which performs a block floating-point arithmetic by auto scaling means. Further, in accordance with the magnitude of a digital signal by an i-bit A/D conversion a suitable j-bit (where $i>j$) digital value is selected for each fixed number of samples input data and a fast Fourier transform of j-bit data is carried out.

BRIEF DESCRIPTION OF THE DRAWINGS

FIGS. 10A to 10F show a timing chart illustrating an example of the operation of the entire apparatus of the present invention;

FIGS. 12A to 12E are diagrams showing the flow of an operation in a Butterfly operation unit.

DESCRIPTION OF THE PREFERRED EMBODIMENTS

Figure 1:
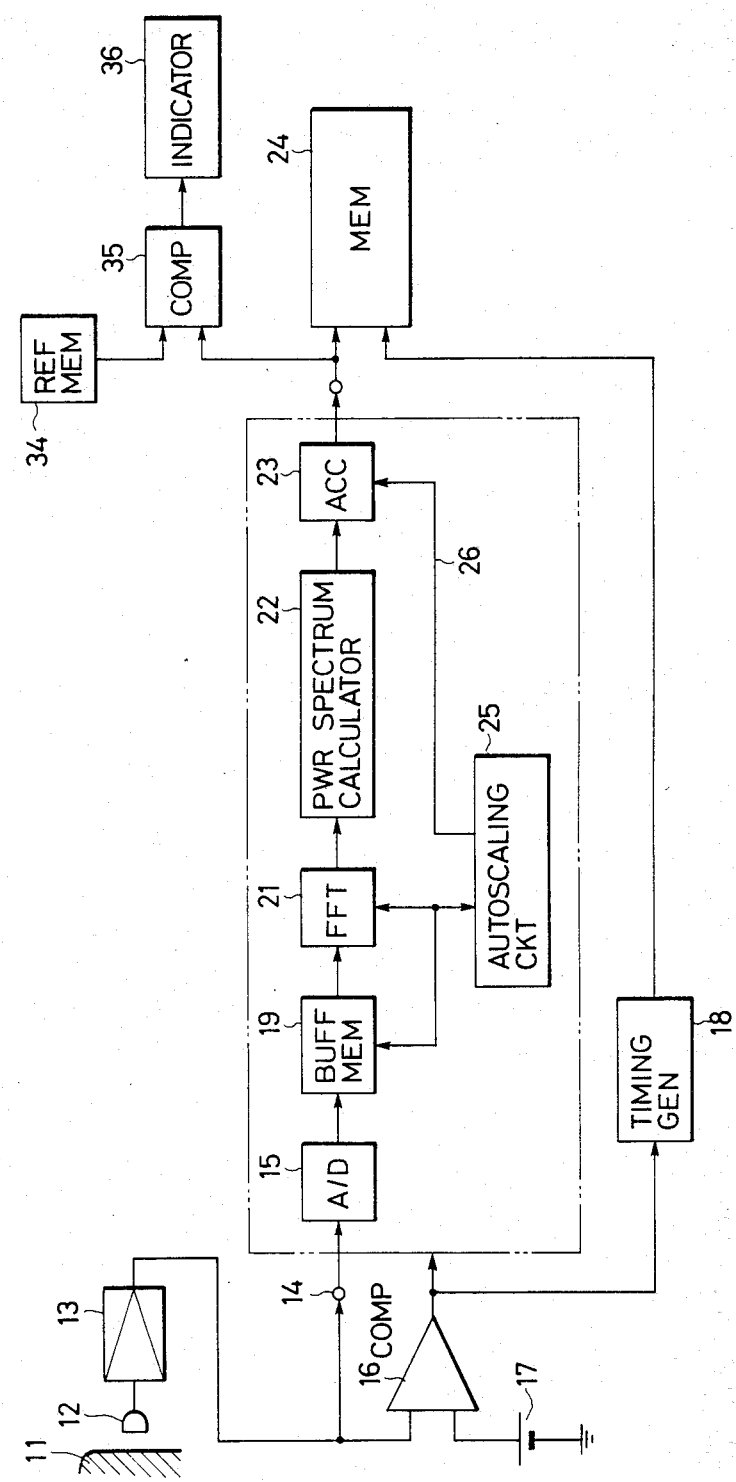
FIG. 1 is a block diagram illustrating an example of the arrangement of the micro fracture detector of the present invention.

FIG. 1 illustrates an embodiment of the present invention, in which an AE signal resulting from micro fracture of an object under investigation 11 is detected as an electrical signal by means of a pickup 12. The output of the pickup 12 is amplified by an amplifier 13 and input via a terminal 14 into an A/D converter 15. In this embodiment the output of the amplifier 13 is provided to a comparator 16, too, wherein it is compared with a reference signal from a reference signal source 17. When the absolute value of the input to the comparator 16 is larger than the reference signal, it is decided that the AE signal has been input, and the A/D converter 15 and the following stages are caused to start their operation and, at the same time, a timing generator 18 is started, indicating the lapse of time.

The A/D converter 15 samples the input AE signal with a fixed period and converts each sampled value into a digital signal of plural bits. The digital signal is written into a buffer memory 19, from which it is transferred to a fast Fourier transform (hereinafter referred to as FFT) processor 21. A complex frequency spectrum output of the FFT processor 21 is converted by a power spectrum calculator 22 into a power spectrum for input to an accumulator 23. If one AE signal is defined as one event, then accumulated power spectrum is calculated for one event and transferred to a memory 24. An auto-scaling circuit 25 computes a scale factor while at the same time controlling a block floating-point arithmetic which takes place in the FFT processor 21. The resulting scale factor 26 is used for standardization of the spectral intensity in the accumulation by the accumulator 23.

In an FFT algorithm with a radix 2, $2^n$ data are defined as one frame, and an FFT operation is conducted for each frame. For example, in the case of n=10, 1024 data constitute one frame. Further, according to the sampling theorem, the spectrum by FFT is not established unless the signal to be measured is sampled at a sampling frequency at least twice higher than the highest frequency contained in the signal to be measured. When the AE signal has a frequency component of 1 MHz, the sampling frequency ($f_s$) is 2 MHz. Accordingly, the time ($T_f$) necessary for inputting data of one frame can be obtained as expressed by the following equation (1):

$$T_f = 2^n/f_s = 1024 \times 10^6 = 0.512 \text{ msec} \tag{1}$$

Figures 2, 6:
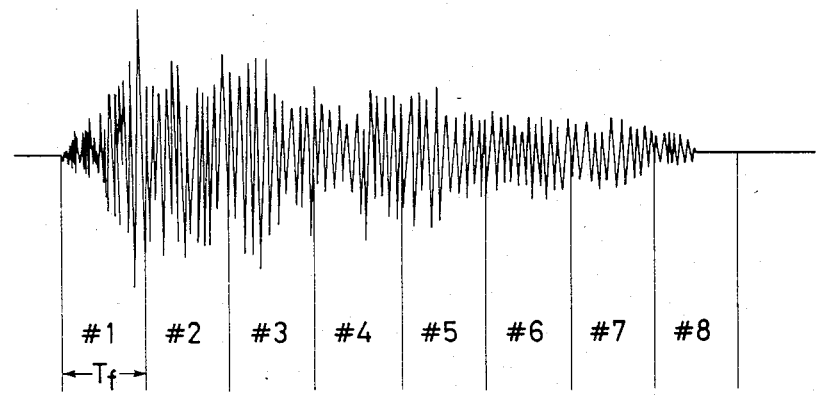
FIG. 2 is a schematic diagram showing the framing of the AE signal.
FIG. 6 is a table showing the relation between signals for controlling respective parts of an arithmetic unit 41 and microinstructions.

FIG. 2 schematically shows the division of the AE signal into frames. There are two FFT methods for the AE signal of longer duration than the time $T_f$ as shown in FIG. 2; the one method is to perform the FFT of one frame of 8192 sample points (n=13), and the other method is to perform the FET for each of eight-divided frames and to accumulate the resulting spectral components, obtaining the spectrum. The example depicted in FIG. 2 employs the latter method for such reasons as follows:

i. The quantity of hardware used is small.
ii. In the case of the AE signal, not so high frequency resolution is needed.
iii. Owing to the averaging operation by the accumulation, micro oscillation of the spectrum peculiar to the FFT is suppressed.

It is also possible, however, to employ the former method.

The operational algorithm of the FFT processor 21 is based on the Cooly-Tukey method, which is disclosed in J. W. Cooly and J. W. Tukey, "An Algorithm for the Machine Calculation of Complex Fourier Series", Mathematics of Computation, 9, pp 297, 1965 and W. T. Cochran et al, "What is the Fast Fourier Transform?", IEEE Trans. Au-15, Vol. 2, pp 48, 1967.

Figure 3:
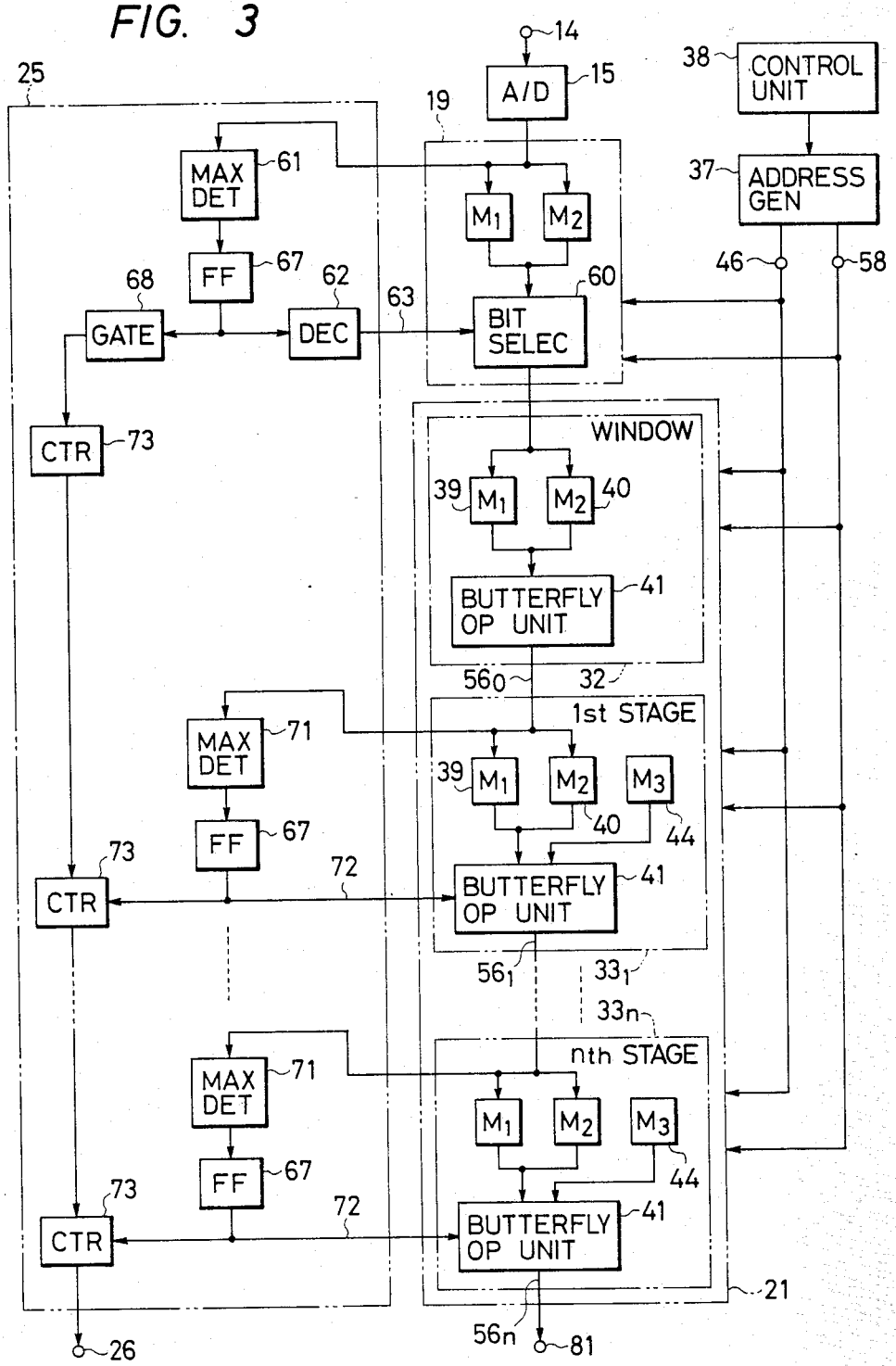
FIG. 3 is a block diagram illustrating, by way of example, a fast Fourier transform processor and an auto scaling circuit 25.
Figure 4:
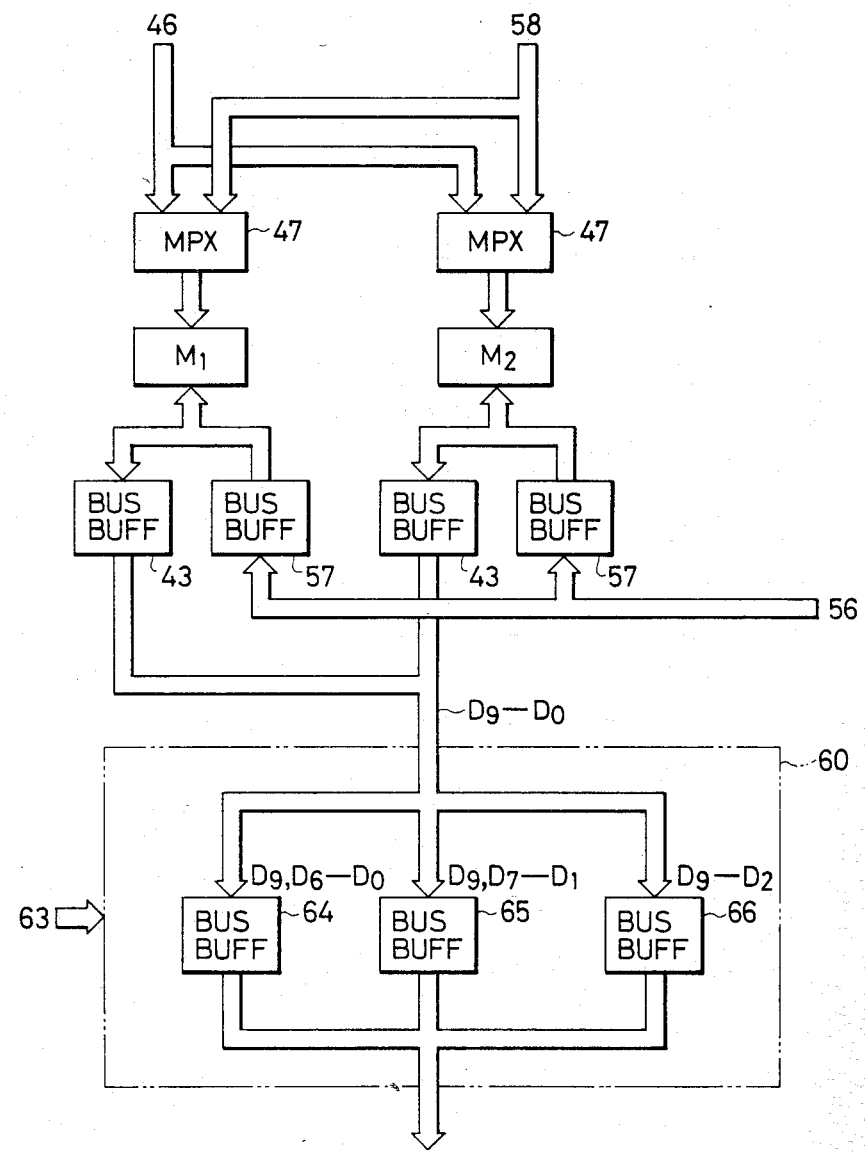
FIG. 4 is a block diagram illustrating an example of a buffer memory 19.
Figure 5:
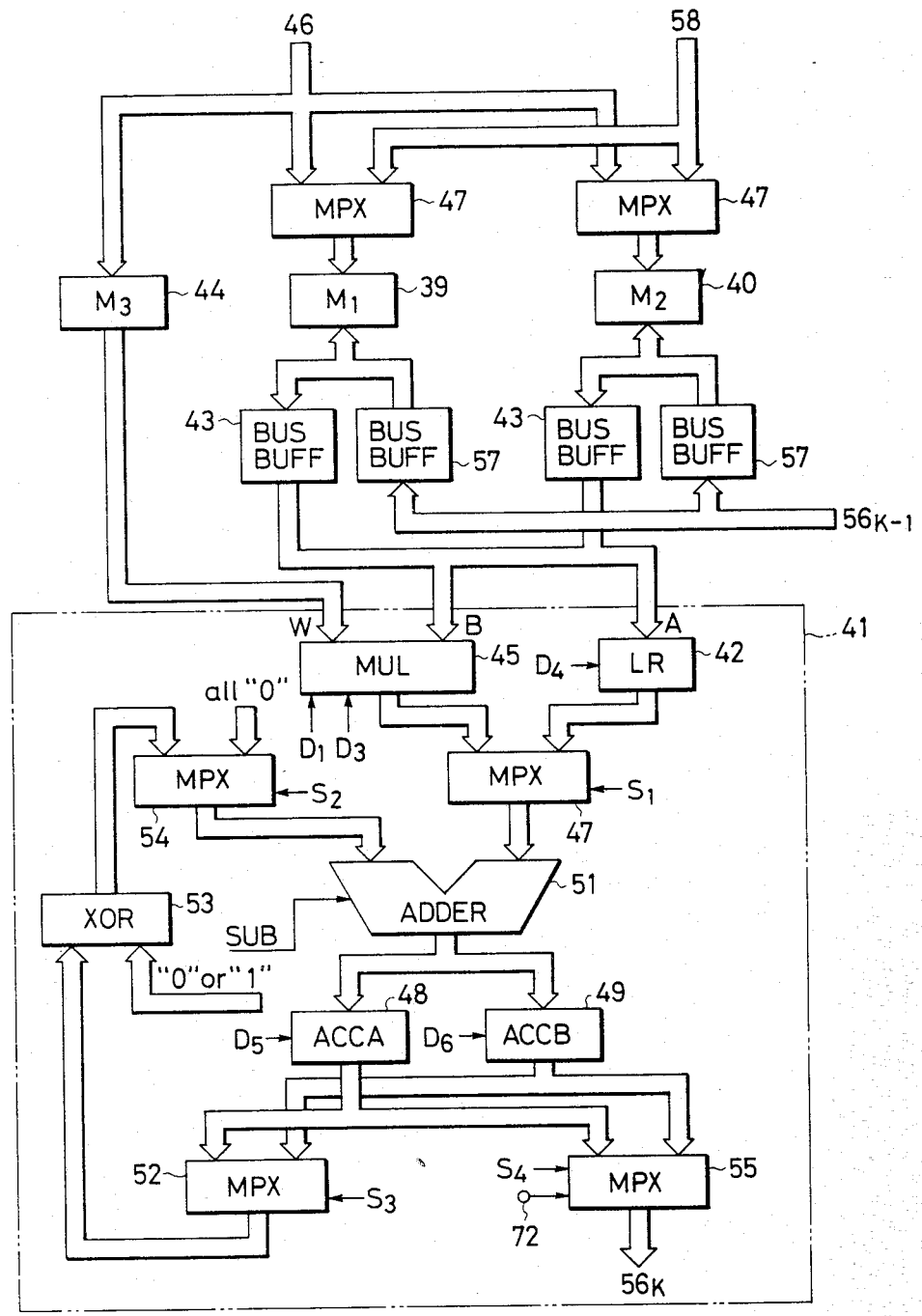
FIG. 5 is a block diagram illustrating an example of an arithmetic stage 33 for performing Butterfly operation.

Assuming that $2^n$ points constitute one frame, as shown in FIG. 3, the FFT processor 21 comprises n Butterfly operation stages $33_1$–$33_n$ and a stage 32 provided at the preceding stage thereof for window processing. In the case of 1024 sample points with n=10, the FFT processor 21 comprises a total of 11 cascade-connected stages 32 and $33_1$–$33_n$. FIG. 4 shows in block form the buffer memory 19 used in FIGS. 1 and 3, and FIG. 5 shows the stage 33 representing one of $33_1$ to $33_n$. The buffer memory 19 and the stages 32 and 33 are each provided with two memories $M_1$ and $M_2$, which are adapted so that when either one of them is in the write state in which the output data of the A/D converter 15 or the preceding stage is written thereinto, the other is held in the readout state in which data written thereinto previously is subjected to an arithmetic operation and transferred to the next stage. Upon completion of the transfer of data at the 1024 sample points, the states of the memories $M_1$ and $M_2$ are inverted relative to each other; namely, the memory held in the readout state is put into the write state and the memory held in the write state is altered to the readout state. Thus the data flows on the basis of the pipelined architecture. In this case, addresses for accessing the memories are supplied from an address generator unit 37.

A Butterfly operation unit 41 in each stage 33 is also controlled by a microinstruction from a control unit 38, performing the Butterfly operation by a pipeline operation. In each stage 33 is provided a memory 44 which has stored therein a rotation vector. Letting input data be represented by A and B, output data be represented by A' and B' and the rotation vector be represented by W in each stage, the Butterfly operation in each stage is a repetition of the following equation (2):

$$A' = A + WB$$
$$B' = A - WB \tag{2}$$

Figures 7, 8:
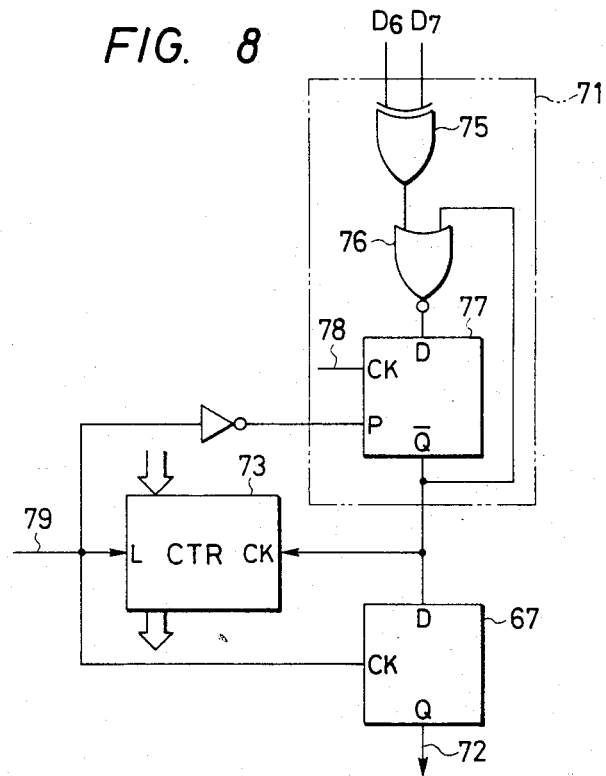
FIG. 7 is a table showing, by way of example, the contents of the instructions shown in FIG. 6.
FIG. 8 is a logical circuit diagram illustrating a specific example of an auto scaling circuit in the operation stage.

At this time, microinstructions are given in such a stage as shown in FIG. 6 and, by decoding the instructions, control signals $D_1$, $D_3$ to $D_6$, $S_1$ to $S_4$ and SUB are created as shown in FIG. 6, executing instructions of such contents as depicted in FIG. 7. In consequence, as illustrated in FIG. 5, the input A in the data read out from one of the memories $M_1$ and $M_2$ through the use of such instructions are loaded via bus buffers 43 into a register 42 and a multiplier 45, respectively, and the rotation vector W is loaded from the ROM 44 into the multiplier 45, performing a multiplication. At this time, a read address 46 is provided to the ROM 44 and, at the same time, it is selected by one of multiplexers 47 for input into that one of the memories $M_1$ and $M_2$ which is to be read out. The multiplication result WB by the multiplier 45 is loaded into a register 48 or 49 via a multiplexer 47 and an adder 51. The multiplication result WB is provided to the adder 51 via a multiplexer 52, an exclusive OR circuit 53 and a multiplexer 54. In this case, bits of one of the inputs to the exclusive OR circuit 53 are all made "0s" or "1s" and, in the former case, the output of the exclusive OR circuit 53 and the content of the register 43 are added to obtain the output data A' and, in the latter case, a "1" is further added to the abovesaid addition result to obtain the complement of WB, providing the output data B'. As a result of this, data are input to control respective parts so that the Butterfly operation of Eq. (2) may be performed in the pipelined fashion. The operation result is provided to the next stage via the register 48 or 49 and an overflow preventing circuit 55 which is also constructed as a multiplex. The memories $M_1$ and $M_2$ are written into by providing thereto data 56 via bus buffers 57 while at the same time selecting an address to be written into 58 by the multiplexers 47. FIGS. 12A to 12E show the flow of the pipelined operation in the Butterfly operation unit 41. In FIGS. 12A to 12E, Re(A), Re(B) and Re(W) indicate the real parts of A, B and C, respectively, and Im(A), Im(B) and Im(W) indicate the imaginary parts of A, B and W, respectively. The Butterfly operation of Eq. (2), rewritten to include the real and imaginary parts, becomes as follows:

$$Re(A') = Re(A) + [Re(B) \cdot Re(W) - Im(B) \cdot Im(W)]$$

$$Im(A') = Im(A) + [Im(B) \cdot Re(W) \cdot Re(B) \cdot Im(W)]$$

$$Re(B') = Re(A) - [Re(B) \cdot Re(W) - Im(B) \cdot Im(W)]$$

$$Im(B') = Im(A) - [Im(B) \cdot Re(W) + Re(B) \cdot Im(W)]$$

Further, MR indicates a register for holding the multiplication result in the multiplier 45.

With such a pipelined arrangement, it is possible to perform a real-time operation as fast as 1.4 MHz in terms of the nyquist frequency, permitting real-time FFT of the AE signal.

One of the features of the AE signal is that individual events may sometimes scatter in intensity over as wide a range as 40 dB or more. Further, the AE signal waveform itself is also a damped oscillation waveform and the data of respective frames in one event are different in magnitude, so that when the AE signal is divided into frames, the data contained in the last frame becomes small in amplitude. Accordingly, in the case of performing a digital operation of a limited word length, it is necessary to employ a method of selecting the word length of the A/D converter 15 longer than that of the digital operation and selecting therefrom suitable bits according to the input signal intensity and a method of preventing an overflow and an underflow during operation by auto scaling means so that sufficient operation accuracy can be obtained even for the small-amplitude signal without missing significant bits.

FIG. 3 illustrates the auto scaling circuit 25. Assuming, for example, that the word length of the A/D converter 15 is 10-bit and that the FFT data has a word length of eight bits. In the buffer memory 19, as shown in FIG. 4 in which the parts corresponding to those in FIG. 5 are identified by the same reference numerals, when 10-bit ($D_9$ to $D_0$) data of one frame is written in one of the memories $M_1$ and $M_2$ from the A/D converter 15, a maximum value in the frame is detected by a maximum value detector 61 (FIG. 3) and, for each frame, the detected output is set in a flip-flop 67, the set content of which is decoded by a decoder 62, and the buffer memory 19 is controlled by the output of the decoder 62 as follows: Since the maximum value that can be represented by 10 bits including a sign bit is 1023, if the maximum value detected by the detector 61 is 255 (1023/4=255) or less, then a bus buffer 64 in FIG. 4 is selected by a bit select signal 63 from the decoder 62 in a bit selector 60 of the buffer memory 19. When the maximum value detected by the detector 61 is in the range of 256 to 511 (=1023/2), a bus buffer 65 is selected and when the detected maximum value is 512 or more, a bus buffer 66 is selected. And the content of the selected bus buffer is transferred as 8-bit data to the FFT processor 21. At the same time, the output of the flip-flop circuit 67 is preset as an initial value of the scale factor 26 in counters 73 via a gate circuit 68. In this way, it is possible to enlarge the dynamic range for the AE input signal of large amplitude variations without necessarily increasing the data word length of the FFT processor 21, that is, the amount of hardware used. Hence, the 8-bit word length can be effectively utilized. Specific examples of the maximum value detector 61, the flip-flop circuit 67 and so forth will be described later on.

Also in each stage 33 of FIG. 3, the block floating-point arithmetic can be controlled through the use of similar means for detecting a maximum value in one frame. The Butterfly operation is as given by Eq. (2) but since $|W| \leq 1$, there is the possibility of an overflow when the data A or B becomes larger than the half of the maximum value represented by eight bits. In the FFT processor 21, the range of the value over which the data A and B may assume is as follows:

$$-128 \leq A, B \leq 127 \tag{3}$$

and, accordingly, it is sufficient to make the data A' and B' as follows:

$$A' = A'/2$$
$$B' = B'/2 \tag{4}$$

only when $$A, B < -64 \text{ or}$$
$$A, B > 63 \tag{5}$$

This is called the block floating-point arithmetic and this method makes it possible to perform the Butterfly operation making the best use of the 8-bit word length. Here, to control whether to divide the data by 2 or not is accomplished by detecting the maximum value of the data input into each Butterfly operation stage 33 by a maximum value detector 71, latching the detected output in a flip-flop circuit 67 and providing it as a block floating-point arithmetic control signal 72 to the overflow preventing circuit 55 (FIG. 5) of each stage. At the same time, the scale factor is stepped by the counter 73 through using the output of the maximum value detector 71 only when the data has been divided by 2. The scale factor propagates through the counters 73 of the respective stages one after another in synchronism with the data flow. Consequently, the scale factor 26 that is finally output as representative of the number of divisions of data by 2 during the FFT operation, and hence it becomes an exponent-indicating quantity using 2 as the base, forming the exponent part of the frequency spectrum. Therefore, during the accumulation, the spectrum of the mantissa part is scaled by the scale factor and accumulated.

FIG. 8 shows a specific example of forming the scale factor. The sixth and seventh bits $D_6$ and $D_7$ in the operation result from the preceding stage are input into an exclusive NOR circuit 75, the output of which is supplied via a NOR circuit 76 to a D flip-flop 77 and input thereinto by a clock 78 for each data. The $\overline{Q}$ output of the flip-flop 77 is fed back thereto via the NOR circuit 76. Consequently, when the data A and B get out of the range A, B < −64 or A, B ≦ 64, the output of the exclusive OR circuit 75 goes to a "1" and the $\overline{Q}$ output of the flip-flop 77 goes to a "1" and thereafter this state is held. When the $\overline{Q}$ output of the flip-flop 77 goes to a "1", the counter 73 is incremented. For each input of the data of one frame (consisting of 1024 samples in this example), the content of the counter 73 of the preceding stage is latched by a clock 79 in the counter 73 and the $\overline{Q}$ output of the flip-flop 77 is latched in the flip-flop 67. The Q output of the flip-flop 67 is delivered as a block floating-point arithmetic control signal 72. The flip-flop 77 is preset by an inverted signal of the clock 79.

Figure 9:
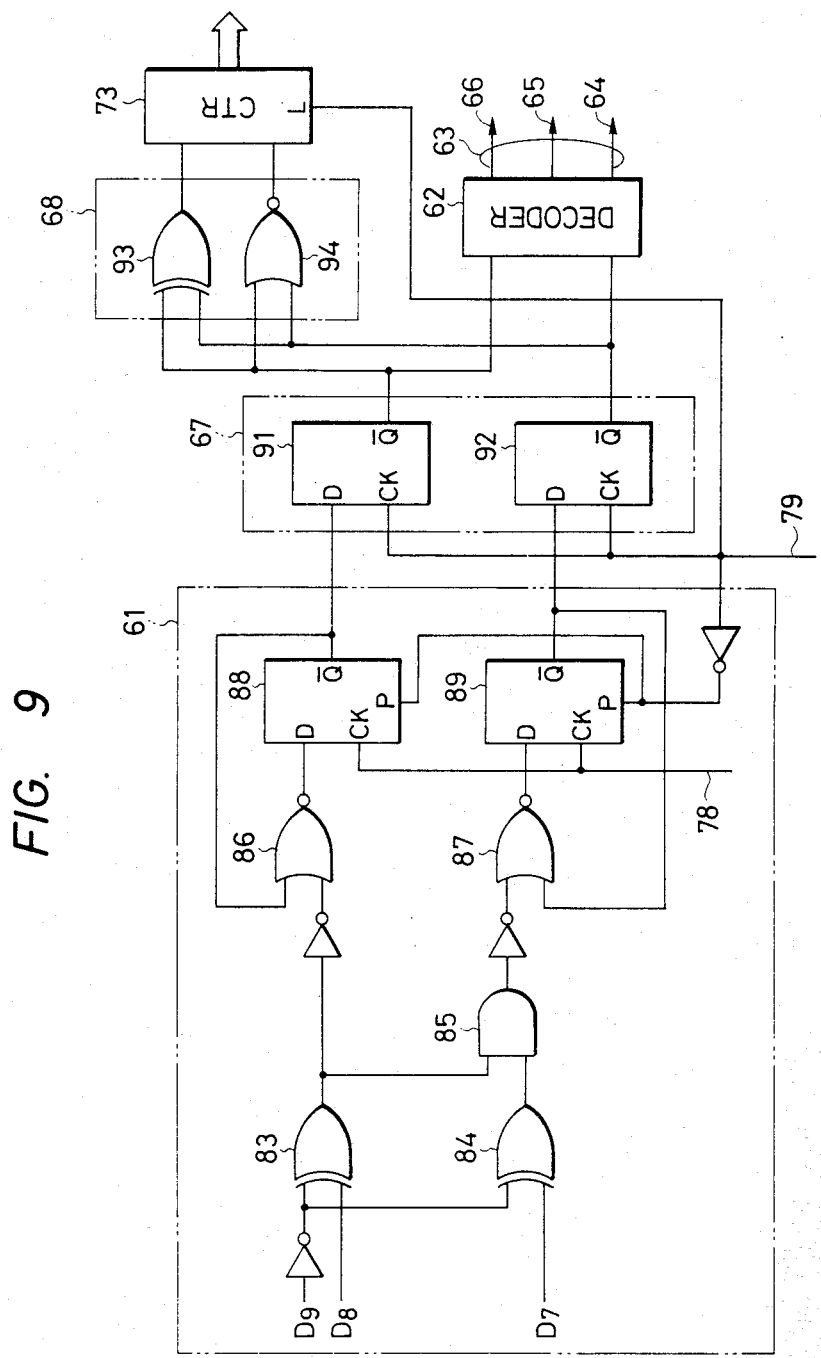
FIG. 9 is a logical circuit diagram illustrating a specific example of the auto scaling circuit at the input of the buffer memory.

The scale factor that is used for data input from the buffer memory 19 to the FFT processor 21 is produced, for example, as shown in FIG. 9. The bits $D_8$ and $D_9$ and the bits $D_7$, $D_8$ and inverted $D_9$ in the 10 bits $D_0$ to $D_9$ ($D_9$ being the most significant bit representing the sign) from the A/D converter 15 are provided to exclusive OR circuits 83 and 84, respectively, the outputs of which are applied to an AND circuit 85, and the output of the circuits 83 and 85 are supplied via inverters to NOR circuits 86 and 87, respectively. The outputs of the NOR circuits 86 and 87 are respectively input by a clock 78 into flip-flops 88 and 89 for each data, and the $\overline{Q}$ outputs of the flip-flops 88 and 89 are fed back to the NOR circuits 86 and 87, respectively. Accordingly, when the input data is more than 255 or less than −256, the $\overline{Q}$ output of the flip-flops 88, 89 go to a "1" and when the input data is more than 127 or less than −128, the $\overline{Q}$ output of the flip-flop 89 goes to a "1". The $\overline{Q}$ outputs of the flip-flops 88 and 89 are input by a clock 79 into flip-flops 91 and 92 for each frame, and their $\overline{Q}$ outputs are decoded by the decoder 62, which provides an output "1" on one of three output lines 63 in accordance with the three states described previously in respect of FIG. 4. In the case where the input data is between −128 and 127, the $\overline{Q}$ outputs of the flip-flops 91 and 92 are both "1", providing an output "1" on the output line 63 connected to the bus buffer 64 in FIG. 4; when the input data is within the range of 128 to 255 or −256 to −129, the $\overline{Q}$ output of the flip-flop 91 is a "1" and the $\overline{Q}$ output of the flip-flop 92 is a "0", providing an output "1" on the output line 63 connected to the bus buffer 65; and when the input data is 256 or more or −257 or less, the $\overline{Q}$ output of the flip-flop 91 is a "0" and the $\overline{Q}$ output of the flip-flop 92 is a "0", providing an output "1" on the output line 63 connected to the bus buffer 66. The $\overline{Q}$ outputs of the flip-flops 91 and 92 are supplied to an exclusive OR circuit 93 and a NOR circuit 94, too. When the input data is 256 or more or −257 or less, the outputs of the circuits 93 and 94 go to a "0" and a "1", respectively; when the input data is within the range of 128 to 255 or −256 to −129, the outputs of the circuits 93 and 94 go to a "1" and a "0", respectively; and when the input data is between 127 and −128, the outputs of the circuits 93 and 94 both go to "0s". The outputs of the circuits 93 and 94 are preset in a counter 73 for each frame, with the latter as the least significant bit; namely, any one of binary numbers 2, 1 and 0 is preset in accordance with the state of the input data.

By providing a register between adjacent ones of the counters 73 as required in FIG. 3, it is possible to prevent the content of the first-stage counter from racing directly to the final-stage counter. Also in the window processing stage 32 shown in FIG. 3, the window processing is performed by a Butterfly operation unit of the same construction as the Butterfly operation unit 41 shown in FIG. 5.

FIG. 10 shows a timing chart of a specific example of the present invention. For instance, data of a first frame #1 of the AE signal shown in FIG. 10A is written into the buffer memory 19 in a section 1 of a time scale (FIG. 10F) and, in a section 2, it is subjected to window operation in the window operation stage 32 as shown in FIG. 10B and then subjected to Butterfly operation in the 10-stage Butterfly operation stage 33, thereafter being output as a complex spectrum 81 in a section 12 (FIG. 10C). Since this spectrum is a back-to-back spectrum peculiar to the FFT operation, only its first half part is converted as a power spectrum in a section 13 (FIG. 10D). Thereafter it is transferred to the accumulator 23 (FIG. 1) and the accumulation is repeated for each frequency component and then the accumulated output is provided as an accumulated power spectrum in a section 17 in which all operations for one event have been completed (FIG. 10E).

Figure 11A:
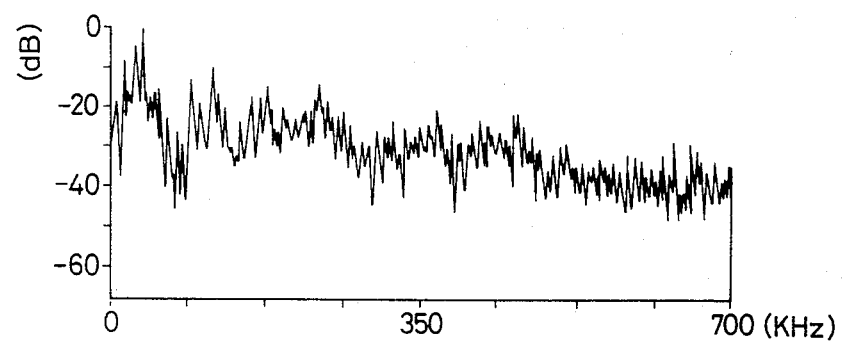
FIG. 11A is a diagram showing an example of the spectrum of the AE signal obtained with an embodiment of the present invention.
Figure 11B:
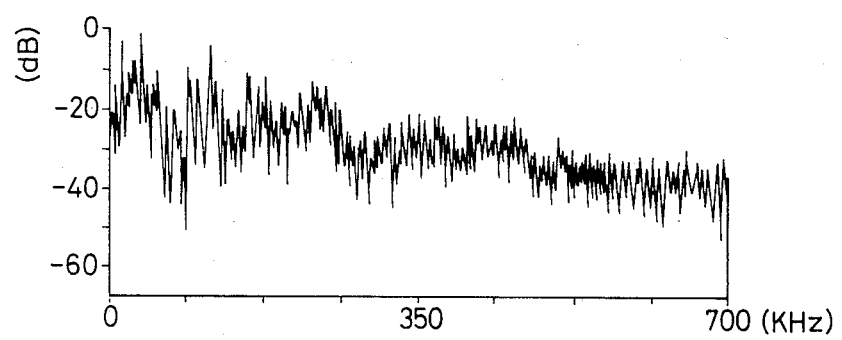
FIG. 11B is a diagram showing an example of the spectrum obtained in the case where the fast Fourier transform was performed at 8192 sample points without framing the AE signal.
Figure 11C:
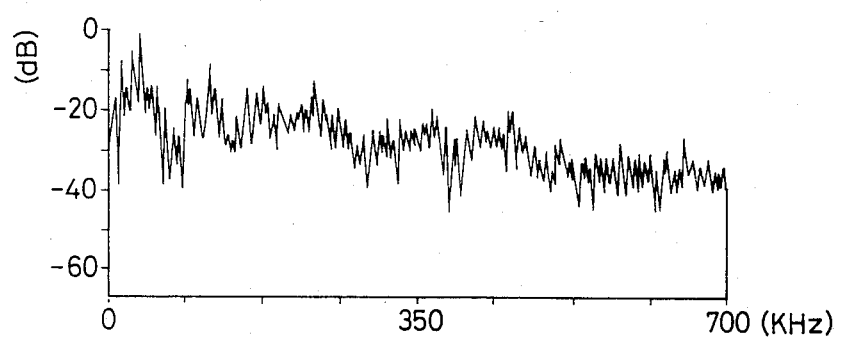
FIG. 11C is a diagram showing an example of the spectrum obtained in the case where the fast Fourier transform of a 14-bit word length of a fixed-point arithmetic without involving the use of the auto scaling circuit 25 was performed.
Figure 12E:
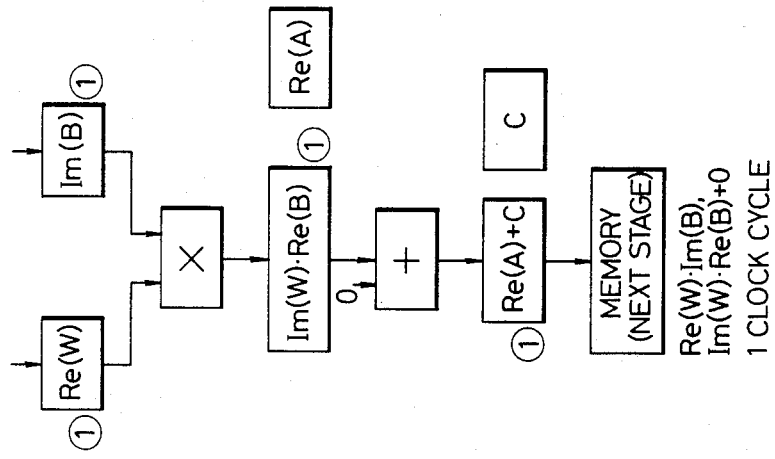
Figure 12D:
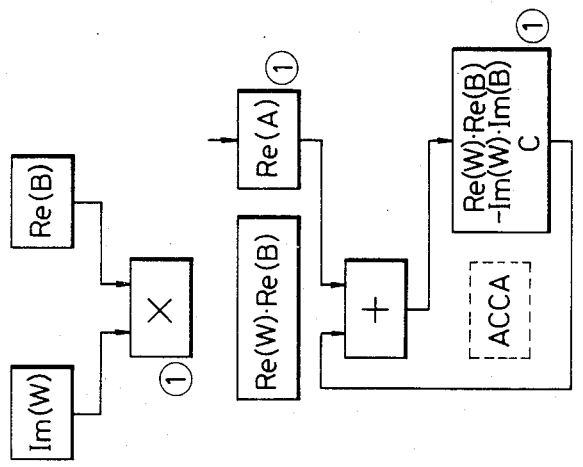

FIG. 11 shows power spectra of the AE signal obtained with the present invention. FIG. 11A shows the spectrum of the AE signal obtained in the case where the framing and the auto scaling were effected; FIG. 11B shows the spectrum obtained by performing the FFT of 8192 sample points without the framing; and FIG. 11C shows the spectrum obtained by 14-bit fixed-point arithmetic FFT without involving the auto scaling means. From the foregoing embodiment it will be understood that the framing does not destroy the features of the AE signal spectrum but rather suppresses its minute variations observed in FIG. 11B to facilitate the discrimination of its features. Further, it is also seen that the provision of the auto scaling circuit 25 makes the 8-bit FFT comparable to the 14-bit fixed-point arithmetic FFT. However, the auto scaling circuit 25 need not always be provided.

With such an arrangement as described in the foregoing, it is possible to make a real-time frequency analysis of an AE signal the amplitude and duration of which greatly differ with events and the frequency component of which ranges over as wide a band as 1 MHz. As illustrated in FIG. 1, the envelope of the frequency spectrum of the thus analyzed AE signal and a reference frequency spectrum pattern prestored in a reference memory 34 are compared by a comparator 35 and when a micro fracture is detected, or when the micro fracture is larger than a predetermined value, an indicator 36 provides a display or gives a warning. In the case of storing the output of the accumulator 23 in the memory 24, the timing signal of the timing generator 18 is also stored in the memory 24 to indicate variations in the generated spectral power with time. In the case where the output of the accumulator 23 is stored in the memory 24 only when the AE signal is obtained through the use of the comparator 16, the memory 24 can be used effectively. Incidentally, the auto scaling circuit 25 is applicable not only to the AE signal frequency analysis but also to other general FFT operations.

It will be apparent that many modifications and variations may be effected without departing from the scope of the novel concepts of the present invention.

What is claimed is:

1. A micro fracture detector comprising:

a pickup for sensing, as an electric signal, an acoustic emission resulting from a micro fracture of an object;

an amplifier connected to the pickup, for amplifying the output of the pickup;

an A/D converter connected to the amplifier, for sampling the amplified output with a fixed period and converting each sampled value into a digital signal;

a fast Fourier transform processor comprised of a cascade connection of a plurality of stages, each including first and second input memories, a third memory having stored therein a rotation vector and an arithmetic unit for performing a Butterfly operation through using a pipelined architecture;

control means for controlling the fast Fourier transform processor so that one of the first and second input memories and the third memory are read out to perform the Butterfly operation through using the pipelined architecture and the operation result is written into that one of the first and second input memories of the next stage which has not been read out, thereby to perform a pipelined operation by all the stages as a whole, and for writing the digital signal from the A/D converter into the first and second input memories alternately for each fixed number of sampling operations;

address generating means for generating a common address for accessing the memories of each stage; and means for calculating the power of each spectral component obtained as the operation result of the last one of the stages to obtain a signal corresponding to the fracture.

2. A micro fracture detector according to claim 1, which includes means for dividing the electric signal of one acoustic emission into a plurality of frames of a fixed period, performing fast Fourier transform for each frame by the fast Fourier transform processor through using the pipelined architecture, and accumulating, for each frequency component, the power of spectra of the respective frames obtained by the fast Fourier transform.

3. A micro fracture detector according to claim 2, wherein the fast Fourier transform processor is caused by auto scaling means to perform a block floating-point arithmetic, by which an exponent part and a mantissa part are calculated separately.

4. A micro fracture detector according to claim 3, wherein the auto scaling means are provided for each stage and is comprised of a maximum value detector for detecting that data input into the stage exceeds the half of the maximum value that the data can take with its bit length in one frame, an overflow preventing circuit for reducing, by the detected output of the maximum value detector, the data output from the stage by half, a scale factor counter stepped by one by the detected output of the maximum value detector, and means for transferring the count value of the scale factor counter to the scale factor counter of the next stage for each frame, whereby the exponent part is obtained from the count value of the scale factor counter of the last stage.

5. A micro fracture detector according to claim 4, wherein the number of bits to be converted by the A/D converter is selected larger than the word length for operation by the fast Fourier transform processor, and which includes bit select means for selecting the data corresponding to the operation word length from the converted output of the A/D converter in accordance with the maximum value in one frame and supplying the selected data to the fast Fourier transform processor.

6. A micro fracture detector according to claim 5, wherein the bit select means is comprised of first and second buffer memories into which the converted output of the A/D converter is written alternately every other frame, means for deciding the range to which the maximum value of the converted output in one frame belongs, a bit selector for selecting, in accordance with the decision result, the bits of the predetermined operation word length from the output read out of that one of the first and second buffer memories into which the converted output is not written and supplying the selected bits to the fast Fourier transform processor, and means for presetting the scale factor corresponding to the decision result in the scale factor counter of the first one of the stages.

7. A micro fracture detector according to any one of claims 1 to 6, wherein the arithmetic unit is comprised of a multiplier for multiplying a part of the data read out from one of the first and second memories and the rotation vector read out from the third memory, a first register for loading the other part of the data read out from one of the first and second memories, a first multiplexer for selecting one of the multiplication result by the multiplier and the content of the first register, an adder supplied at the one input side with the output of the first multiplexer, third and fourth registers respectively supplied with the output of the adder, a second multiplexer for selecting one of the outputs of the third and fourth registers, an exclusive OR circuit for XOR-ing the output of the second multiplexer and a given "1" or "0", a third multiplexer for selectively supplying one of the output of the exclusive OR circuit and a "0" to the other input side of the adder, and a fourth multiplexer for selectively outputting one of the outputs of the third and fourth multiplexers to the next stage.

8. A micro fracture detector according to any one of claims 1 to 6, which includes, as a first stage of the fast Fourier transform processor, a stage for performing window processing.

9. A micro fracture detector according to any one of claims 1 to 6, which includes means for comparing the envelope of the obtained power spectrum and a reference power spectrum to detect a micro fracture from the comparison result.

10. A micro fracture detector according to any one of claims 1 to 6, wherein the electric signal from the pickup is supplied to the comparator, and which includes means for deciding the arrival of the acoustic emission when the electric signal exceeds a predetermined level and starting the fast Fourier transform processor.

11. A micro fracture detector according to claim 10, which includes a timing generator started by the output of the comparator.

* * * * *